United States Patent
Benlloch Baviera et al.

(10) Patent No.: US 11,147,523 B2
(45) Date of Patent: Oct. 19, 2021

(54) PET IMAGING DEVICE FOR OBSERVING THE BRAIN

(71) Applicants: General Equipment for Medical Imaging, S.A., Valencia (ES); Consejo Superior de Investigaciones Cientificas, Madrid (ES); Universitat Politècnica de Valencia, Valencia (ES)

(72) Inventors: José María Benlloch Baviera, Valencia (ES); Antonio Javier González Martínez, Valencia (ES); Laura Moliner Martínez, Valencia (ES); Juan Vicente Catret Mascarell, Valencia (ES); Carlos Correcher Salvador, Valencia (ES)

(73) Assignees: General Equipment for Medical Imaging S.A.; Consejo Superior de Investigaciones Científicas; Universitat Politécnica de València

(*) Notice: Subject to any disclaimer, the term of this patent is extended or adjusted under 35 U.S.C. 154(b) by 0 days.

(21) Appl. No.: 16/901,691

(22) Filed: Jun. 15, 2020

(65) Prior Publication Data
US 2020/0305811 A1 Oct. 1, 2020

Related U.S. Application Data

(63) Continuation-in-part of application No. 16/169,075, filed on Oct. 24, 2018, now Pat. No. 10,716,520, (Continued)

(30) Foreign Application Priority Data

Apr. 25, 2016 (ES) .............................. ES201630524

(51) Int. Cl.
*A61B 6/03* (2006.01)
*A61B 6/00* (2006.01)
(Continued)

(52) U.S. Cl.
CPC ............ *A61B 6/4258* (2013.01); *A61B 6/037* (2013.01); *A61B 6/08* (2013.01); *A61B 6/4275* (2013.01);
(Continued)

(58) Field of Classification Search
CPC ......... A61B 6/037; A61B 6/08; A61B 6/4258; A61B 6/4275; A61B 6/466; A61B 6/501;
(Continued)

(56) References Cited

U.S. PATENT DOCUMENTS 9,226,717 B2 1/2016 Tashima et al.
2010/0288935 A1 11/2010 Majewski et al.
(Continued)

FOREIGN PATENT DOCUMENTS

WO 2010/033159 A1 3/2010

OTHER PUBLICATIONS

S. Yamamoto et al.; "Development of a Brain PET System, PET-Hat: A Wearable PET System for Brain Research"; IEEE Transactions on Nuclear Science; vol. 58, pp. 668-673, Jun. 2011;—(6) pages.

*Primary Examiner* — Mark R Gaworecki
(74) *Attorney, Agent, or Firm* — Boyle Fredrickson, SC

(57) ABSTRACT

A PET imaging device for observing a brain includes a hollow three-dimensional structure with a shape capable of housing a head. The PET imaging device comprising multiple independent gamma ray detection modules that together form a structure capable of surrounding the head, said detection modules comprise continuous scintillation crystal blocks, wherein "continuous" means that the crystal blocks can be continuous in one or in two directions, each of the continuous scintillation crystal blocks has a polygonal main cross-section, and said structure is an elongated structure having a major axis in a direction corresponding to the
(Continued)

front-nape direction and a shorter axis in a direction corresponding to a straight line joining ears on the head. The continuous scintillation crystal blocks are positioned adjacent to fit laterally in an exact manner with each other throughout their entire thickness, building a mosaic, without gaps between adjacent crystal blocks and without overlapping each other.

30 Claims, 10 Drawing Sheets

Related U.S. Application Data which is a continuation of application No. PCT/ES2017/070248, filed on Apr. 25, 2017.

(51) Int. Cl.
    *G06T 7/00*     (2017.01)
    *G01T 1/164*     (2006.01)
    *G01T 1/20*     (2006.01)
    *A61B 6/08*     (2006.01)
    *G01T 1/29*     (2006.01)

(52) U.S. Cl.
    CPC .............. *A61B 6/466* (2013.01); *A61B 6/501* (2013.01); *G01T 1/164* (2013.01); *G01T 1/1642* (2013.01); *G01T 1/2985* (2013.01); *G06T 7/0012* (2013.01); *G06T 2207/10104* (2013.01)

(58) Field of Classification Search
    CPC ..... G01T 1/164; G01T 1/1642; G01T 1/2985; G06T 7/0012; G06T 2207/10104
    See application file for complete search history.

(56) References Cited

U.S. PATENT DOCUMENTS

2013/0218010 A1    8/2013    Weinberg et al.
2016/0166219 A1    6/2016    Majewski et al.

PET IMAGING DEVICE FOR OBSERVING THE BRAIN

CROSS-REFERENCE TO RELATED APPLICATIONS

This application is a continuation-in-part of and claims priority to U.S. application Ser. No. 16/169,075, filed on Oct. 24, 2018, which is, in turn, a continuation of and claims priority to PCT Application No. PCT/ES2017/070248, filed on Apr. 25, 2017, which, in turn, claims priority to Spanish Application No. P201630524, filed on Apr. 25, 2016. The entire contents of each of these applications is incorporated herein by reference.

FIELD OF THE INVENTION

The present invention has application in the field of medical devices for diagnostic imaging, specifically in positron emission tomography (PET) devices.

BACKGROUND OF THE INVENTION

Positron Emission Tomography is an "in vivo" diagnostic and research technique for imaging, capable of measuring the metabolic activity of the human body. The PET technique is based on detecting and analyzing the three-dimensional distribution that an ultrashort half-life radiopharmaceutical, administered through an intravenous injection, takes inside the body. Depending on what you want to study, different radiopharmaceuticals are used.

The image is obtained thanks to the fact that the devices are able to detect the gamma photons emitted by the patient. These 511 keV gamma photons are the product of an annihilation between a positron, emitted by the radiopharmaceutical, and a cortical electron from the patient's body. This annihilation gives rise to the emission, essentially, of two photons. For these photons to end up shaping the image they must be detected "in coincidence", that is, at the same time, in an appropriate time period (nanoseconds). In addition, they must come from the same direction and opposite sense of direction, but also their energy must exceed a minimum threshold that certifies that they have not suffered significant energy dispersions in their journey (scatter phenomenon) to the detectors. The detectors of a PET scanner are arranged in a ring-shaped structure around the patient, and because they detect in coincidence the photons generated in each annihilation, they will make up the image. To obtain the image, these detected photons are converted into electrical signals. This information is then subjected to filtering and reconstruction processes, thanks to which the image is obtained.

The dedicated brain PET is useful for the measurement of brain activity and is effective for the early diagnosis of neurodegenerative diseases such as Parkinson's disease or Alzheimer's disease, as well as other mental illnesses such as schizophrenia or severe depression. For an accurate diagnosis high quality images are required, therefore, the device must be designed with high spatial resolution and sensitivity. The sensitivity can be improved by increasing the thickness of the crystals, decreasing the distance of the detector to the patient and/or covering the maximum possible surface of the patient's skull.

Various approaches have been proposed to solve the problem of improving the sensitivity of brain PET, such as patent application WO2010/033159, where Majewski et al. They propose a simple spherical ring around the head to generate the Image. The invention described in this application has the disadvantages that the ring does not cover the entire brain and, having a circular shape, is not optimized for the typically oval shape of the human head. Likewise, in 2011, the article by S. Yamamoto et al. is published in the IEEE Transactions on Nuclear Science (vol. 58, pp. 668 to 673). "Development of a Brain PET system, PET-Hat: A Wearable PET System for Brain Research" where an equally circular and single-ring PET device is described, showing no advance in the aspect of sensitivity with respect to the aforementioned patent. In 2013, Weinberg I. et al described in the patent US2013218010 a multi-ring device of circular section that includes partial rings of detectors, which do not complete the ring, in order to increase the sensitivity. All these works have in common that they are based on rings of circular section using square detectors.

In 2015, Tashima ef al. describe in the U.S. Pat. No. 9,226,717 B2 (US201501 15162 A1) a PET device, of similarly circular section, but organized in the form of a hemisphere instead of a cylindrical one, which incorporates an element not physically coupled to the main hull in order to increase its sensitivity.

The construction of a device that optimizes the sensitivity of a dedicated brain PET, which at the same time minimizes the number of detectors used, would require building a surface that would be completely adapted, in shape and size, to the head, particularly the human head. However, there are important limitations as to how to generate this surface due to the procedure used to manufacture the continuous scintillating crystals that are included in these devices. These limitations are related to the maximum size and shape in which these crystals can be carved.

Further, it is impossible to perform exactly a three-dimensional elongated curved surface (such as an ellipsoid) starting from flat surfaces in the form of polygons. However, although it is not trivial, it is possible to approximate those curved surfaces to a polyhedron constructed from flat surfaces in the form of polygons. The object of the present invention is precisely to achieve a PET imaging device with the maximum angular coverage of the brain by means of independent detection modules of polygonal main section and together constituting a three-dimensional elongated structure adapted to the head, in particular the human head and with ability to be arranged as close as possible to the head, to minimize the number of detectors.

Taking into account the limitations existing in the manufacturing of crystals, and using the regular geometric shapes previously proposed in the state of the art, the device is either too far from the actual geometry of the head (as seen in FIG. 1), or the truncated icosahedron that illustrates the state of the art), or too small due to the number of faces and maximum size of each face (typically 70 mm), as in the case of the truncated icosahedron.

BRIEF DESCRIPTION OF THE INVENTION

The present invention solves the problems of the state of the art by means of a PET device dedicated to the brain with a geometric shape different from those previously proposed and which improves the sensitivity of the equipment with respect to other configurations based on rings or spherical helmets.

Detectors are also proposed with a shape different from the square form (triangular, pentagonal or hexagonal) so that starting from flat surfaces made by several regular polygons the set ideally approximates a sphere.

The device of the present invention comprises detectors with pentagon and hexagon shapes, forming geometries that, unlike other more common forms, such as the truncated icosahedron, allow generating larger diameters of the detector device, for a given maximum size of scintillating crystal. Likewise, they allow generating elongated forms, with non-circular perimeters, better adapted to the morphology of the head, in particular the human head.

The expression "continuous" crystal in this specification is to be understood in a broad sense: "continuous" means that the crystal can be continuous in one direction or in two directions (similar to a slab), wherein "direction" refers to the direction of one of the axes of a Cartesian coordinate system.

"Continuous crystal" means not only crystals with regular cross section, such as squares, but also with shapes in which one dimension is significantly larger than the other such as crystal slabs or semi-monolithic crystals.

"Crystal block" in this specification means a single crystal or a set of several crystals. A single continuous crystal or a set of continuous crystals form a "crystal block". As an example:
- a "crystal block" can be formed by a single crystal with regular main cross-section, such as square main cross-section
- a "crystal block" can be formed by several crystals each one with a rectangular main cross-section and wherein the resulting "crystal block" might have a square main cross-section.

According to the invention the "crystal blocks", that can be formed as explained above, by one or more crystals, are positioned adjacent one to each other to fit laterally in an exact manner throughout their entire thickness, building a mosaic, without leaving gaps between adjacent "crystals blocks" and without overlapping each other.

The "crystal blocks" are continuous in one direction, or in two directions, wherein "direction" refers to the axes of a Cartesian coordinate system. The crystal or crystals forming a "crystal block" are continuous as well.

The essential property defining a "continuous crystal", in this broad sense, is that the depth of interaction of the gamma rays inside the crystal is determined by the width or/and other features of the light distribution measured with the photo-sensors that are allocated just below the crystal and serve as a readout of the scintillated light. The position of at least one of the other two coordinates (the ones along the photo-sensor matrix) of the total of 3 coordinates of the gamma ray impact position is also determined by measuring the center of gravity or/and other features of the light distribution with those photo-sensors. If only one coordinate is determined in such a way, the other one is determined through the finding of which crystal has been hit by the gamma ray, as is done in pixelated crystals.

This definition of "continuous crystal" therefore implies that the impact position of the gamma rays may take any value, both in the depth of interaction and at least one of the other two coordinates, inside the crystal, varying continuously from, and to, all the spatial limits of that crystal. This does not happen with the pixelated crystals since in this case the detector module is not able to determine different positions inside the crystal and the position of all impacts in that crystal is usually assigned to the center of that pixel.

The essential feature of the present patent application is the geometrical configuration used to allocate all the detector modules (also called detector blocks), so that there are no gaps between adjacent "crystal blocks", in order to increase the sensitivity of the brain scanner. The detector modules may consist of one or a plurality of continuous crystals in the broad sense, as defined previously, and such plurality of continuous crystals may (or not) share the same read-out electronics.

Unless otherwise specified in this specification, the information referring to a "crystal" or "continuous crystal" applies to "crystal blocks" as well.

Furthermore, in another configuration of the present patent application two panels formed by detector modules of the brain scanner, may be removed temporally from the brain scanner so that a different part of the body is imaged with those two panels. In a preferred configuration both panels are of identical shape and are flat. Those panels may be extracted, for instance, from the part of the brain scanner corresponding to the top and back part of the head, or from the parts corresponding to the two lateral sides of the head.

The device of the present invention is a PET imaging device dedicated to the observation of the brain, characterized in that as a whole it has a structure with a shape capable of housing a head, comprising independent gamma ray detection modules, said detection modules comprise continuous scintillation crystal blocks of polygonal main section, in which the detection modules together form a hollow three-dimensional structure capable of enclosing the head, and said elongated three-dimensional structure having a major axis in the direction corresponding to the front-nape direction in the direction corresponding to the straight line joining the ears, and the adjacent scintillation crystal blocks being arranged to fit laterally in an exact manner with each other throughout their thickness, constituting a mosaic, that is to say, without leaving gaps and without overlapping each other. Preferably the adjacent scintillation crystal blocks are of the same thickness fitting laterally in an exact manner with one another throughout their entire thickness.

The detection modules may have a square or rectangular shape forming together a lying down, hollow, prism with a rectangular base capable of housing a head, the anterior base of said prism being at the front of the structure capable of being faced to the face of a subject, and the rear base of the prism is in the zone that corresponds to the back of the head, in the posterior part of the structure that can be confronted to the occipital bone. Other alternatives for this embodiment are defined in the dependent claims.

The detection modules may also have a square or rectangular shape forming together a hollow prism of bases of pentagonal, hexagonal, or octagonal section capable of housing a head, the anterior base of said prism being at the front of the structure capable of being facing the face of one subject, and the other base of the prism on the back of the structure would face the back of the head, that could be confronted with the occipital bone.

Additional alternatives relate to a PET imaging device comprising detection modules that are of triangular, square, rectangular shape or combination thereof, which together form a hollow prism with a polygonal dome base, for example square, pentagonal, hexagonal, heptagonal or octagonal.

Additional alternatives refer to a PET imaging device comprising square or rectangular shaped detection modules, forming together a hollow prism capable of housing a head whose bases are formed by polyhedral domes. According to another variant, the detection modules have a square or rectangular shape forming together a hollow octahedral prism capable of housing a head, and with a base in the form of a square dome.

The detection modules can also form a hollow prism whose lateral faces are the faces capable of being arranged between the nape and the forehead, and the bases of the prism are the faces that can be arranged parallel to the ears. For example, the prism can be formed by eight sides including a side that can face the chin of a subject and the absent sides—likely to face the neck and the eye area—and the bases, are formed by a square formed by several detectors, for example 9 detectors.

According to other alternatives, the detector modules can form a three-dimensional hollow structure with an elongated shape, that is also narrower in the anterior part corresponding to the area of the forehead, when the device is in use, than in the posterior part corresponding to the area of the nape, when the device is in use, so that said structure is capable of being adapted to the shape of the head. For example, the detector modules can form a three-dimensional hollow structure comprising 76 vertices or 84 vertices, and have flat surfaces of section, —which in at least part of said detector modules—has a pentagonal or hexagonal section, regular or irregular.

The PET imaging device can further comprise a mechanical matrix with structure that is opaque to visible light, rigid, honeycomb like, where each of the detection modules are housed in their pre-established position and orientation, and a mechanical interface in order that a module can be linked with the other modules. Therefore, the mechanical matrix will cover all the modules, and each one of the modules, in turn, can be encapsulated or not.

In the detection modules, the continuous scintillation crystal blocks can have the same width for all detectors regardless of their polygonal shape.

The PET imaging device can also comprise detector modules with two different sizes.

Alternatively, each detection module has a single face where the photo-detectors are located, and such that the surface opposite to the photo-detection is completely polished and covered by a retro-reflector.

The PET imaging device may also comprise a light diffusing sheet or a light guide between each continuous scintillation crystal block and the photo-detectors.

The detection modules are preferably configured so that the gamma rays enter through the opposite side with respect to the location of the photo-detectors, although they could also be configured so that the gamma rays enter through the face where the photo-detectors are located.

The PET imaging device may also comprise a protective element capable of being mechanically or manually operated to produce a complete adaptation of the PET imaging device to the shape of an object—in particular, a human head—the image of which is to be obtained, and to immobilize said object. The protective element can be an air cushion system, attached to the set of detection modules that by means of an inflation system, filled the separation between the PET image device and the object the image of which is to be obtained, or a system of elastic containers, filled with small spherical particles or with any other geometry, of low density, which when pressed mechanically cause the adaptation of the PET imaging device to the shape of the object whose image is intended to be obtained.

The invention also has as an object a method for performing an image acquisition with a PET imaging device as defined above, which comprises arranging a protective element as the one defined above between the PET imaging device and the object the image of which is to be obtained, (in particular a human head), so that said protective element when being mechanically or manually operated produces a complete adaptation of the PET image device to the shape of the object the image of which is to be obtained. Other alternatives for this embodiment are defined in the dependent claims.

In the present specification, unless explicitly stated otherwise, the term "crystal" is equivalent to the term "continuous crystal". The same applies to "crystal block" and "continuous crystal block".

The expression "detector module" is equivalent to "detection module" or simply "module", unless explicitly stated otherwise.

Right. Reading through rows and columns of the photo-detectors of the figure on the left. The signals from the photo-detectors of each row or column are summed by analog electronics before digitalization. The signals of all the smaller size detectors corresponding to each row or column are also summed together with the corresponding signals of the photo-detectors of large size of the same row or column before digitalization. Analogous arrangements are made in the case that the surface of the continuous scintillation crystal block has the shape of a pentagon, hexagon, etc.

Figure 15:
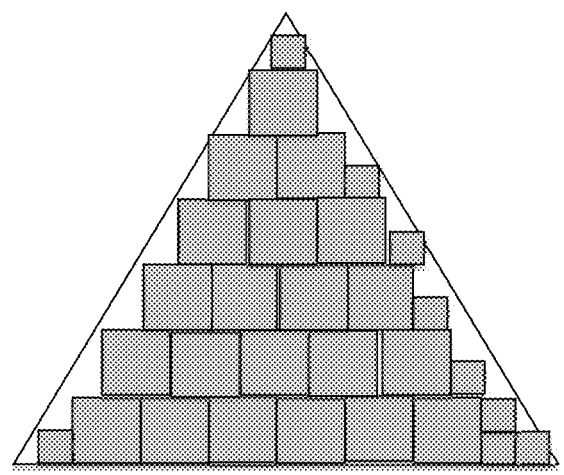

FIG. 15: shows an example of arrangement of the photo-detectors in order to cover a larger area of the scintillating continuous crystal block without the restriction of the alignment in rows and columns. This involves the individual reading of each of the photo-detectors and their digitization by means, for example, of an ASIC (Application Specific Integrated Circuit). This arrangement without alignment restrictions slightly increases the area covered by the photo-detectors. Analogous arrangements are made in the case that the surface of the scintillation crystal block has the shape of a pentagon, hexagon, etc.

Figure 16:
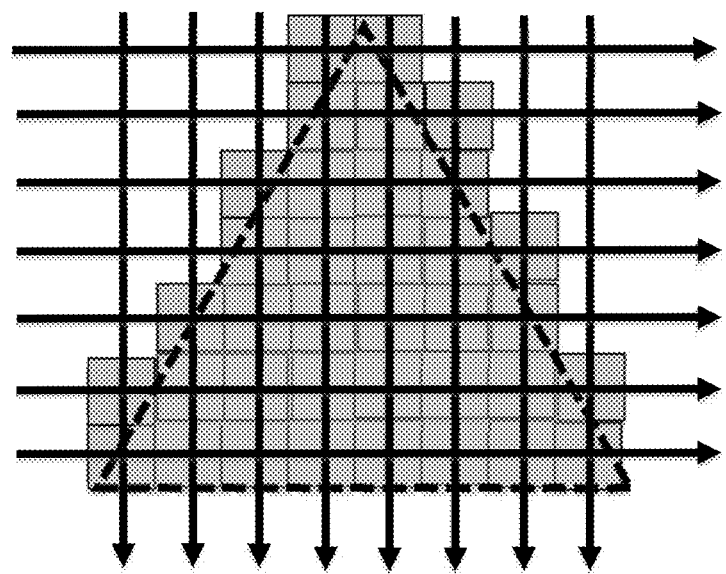

FIG. 16: shows an example of arrangement of the photo-detectors to completely cover the surface of the continuous scintillation crystal block, surpassing the surface area of the triangle. The collision with the photo-detectors of adjacent crystal blocks, if the latter are square or rectangular in section, is avoided by increasing the thickness of the triangular scintillation crystal block, or by slightly shifting (a few millimetres) said crystal block towards the outside or by using a thick sheet of material transparent to light, that acts as a diffuser of light or as a light guide, as shown in the following figures. Analogous arrangements are made in the case that the surface of the continuous scintillation crystal block has the shape of a pentagon, hexagon, etc.

Figure 17:
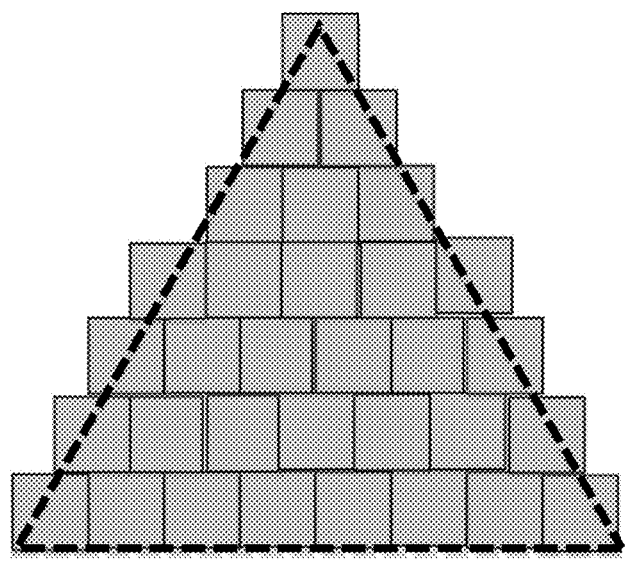

FIG. 17: shows an example of arrangement of the photo-detectors in order to completely cover the surface of the continuous scintillation crystal block, surpassing the surface area of the triangle, without the restriction of the alignment in rows and columns. This involves the individual reading of each of the photo-detectors and their digitization by means, for example, of an ASIC (Application Specific Integrated Circuit). This arrangement without alignment restriction minimizes the number of photo-detectors that are required to completely cover the crystal area. Analogous arrangements are made in the case that the surface of the scintillation crystal block has the shape of a pentagon, hexagon, etc.

Figure 18:
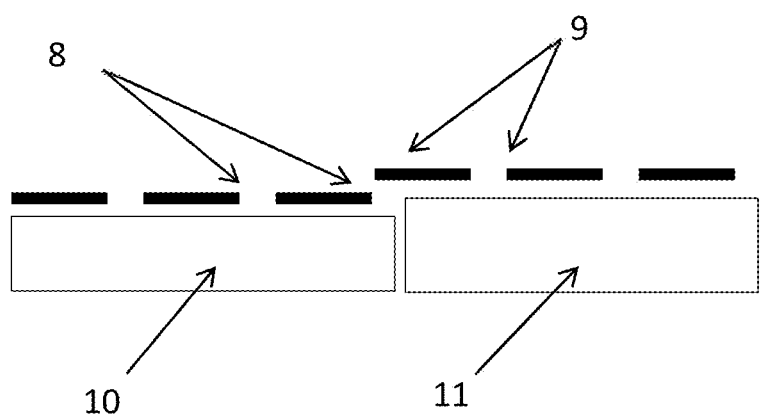

FIG. 18: profile view of two adjacent continuous scintillation crystal blocks, the one on the left with a square or rectangular section and the one on the right with a triangular, pentagonal, hexagonal, etc. section. In a dashed line, the photo-detectors are shown. The photo-detectors (9) associated with the crystal block on the right (11) exceed the surface area of the triangle in order to completely cover the surface of the scintillation crystal block. The collision with the photo-detectors (8) of the glass on the left (10) is avoided because the glass on the right (11) is slightly (a few millimetres) thicker.

Figure 19:
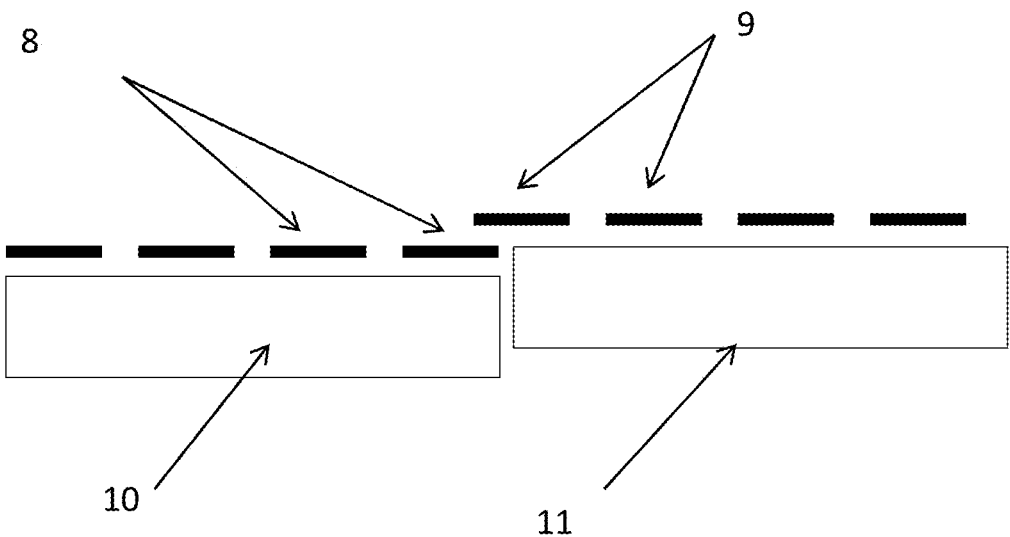

FIG. 19: profile view of two adjacent continuous scintillation crystal blocks, the one on the left with a square or rectangular section and the one on the right with a triangular, pentagonal, hexagonal, etc. section. In a dashed line, the photo-detectors are shown. The photo-detectors (9) associated with the crystal block on the right (11) exceed the surface area of the triangle in order to completely cover the surface of the scintillation crystal block. The collision with the photo-detectors (8) of the crystal block on the left (10)

is avoided because the glass on the right (11) is slightly shifted (a few millimetres) outwards.

Figure 20:
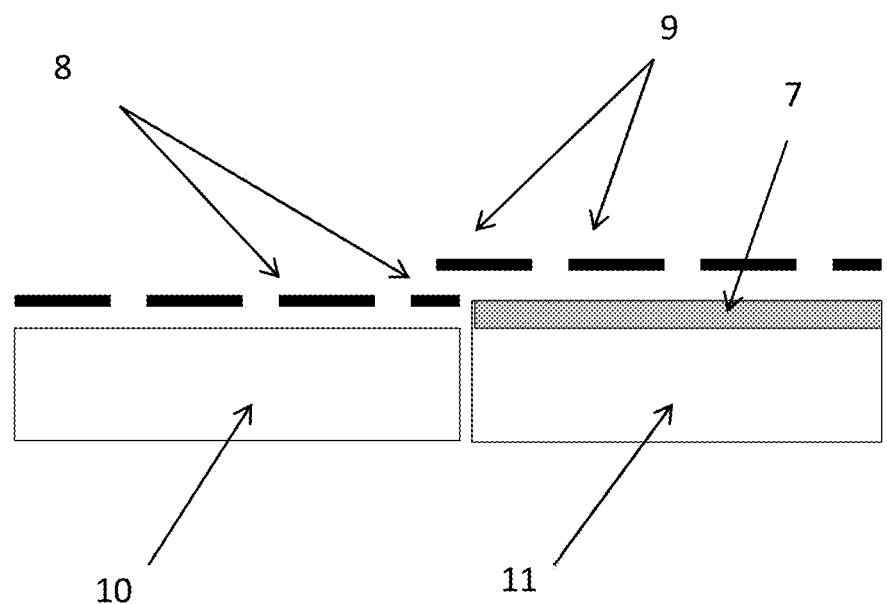

FIG. 20: profile view of two adjacent continuous scintillation crystal blocks, the one on the left with a square or rectangular section and the one on the right with a triangular, pentagonal, hexagonal, etc. section. In a dashed line, the photo-detectors are shown. The photo-detectors (9) associated with the crystal block on the right (11) exceed the surface area of the triangle in order to completely cover the surface of the scintillation crystal block. The collision with the photo-detectors (8) of the crystal block on the left (10) is avoided because a thin sheet (a few millimetres thicker than the glass sheet on the left) of transparent and light diffusing material—or light guide (7)—has been installed between the crystal block on the right (11) and its associated photo-detectors.

Figure 21:
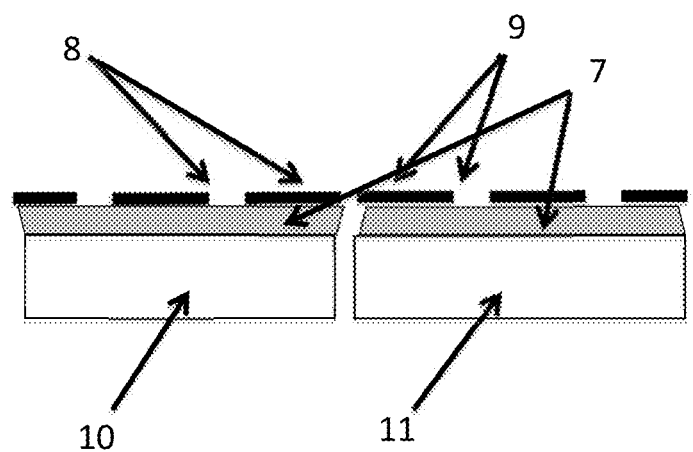

FIG. 21: shows light guides in the form of truncated pyramids (fish tail) with a broader base in the part of the scintillation crystal block (as shown for example in FIG. 21) and with the shape of the polygon of said crystal block, to avoid the collision with the photo-detectors of adjacent crystal blocks, regardless of the shape of the polygon.

Figure 22:
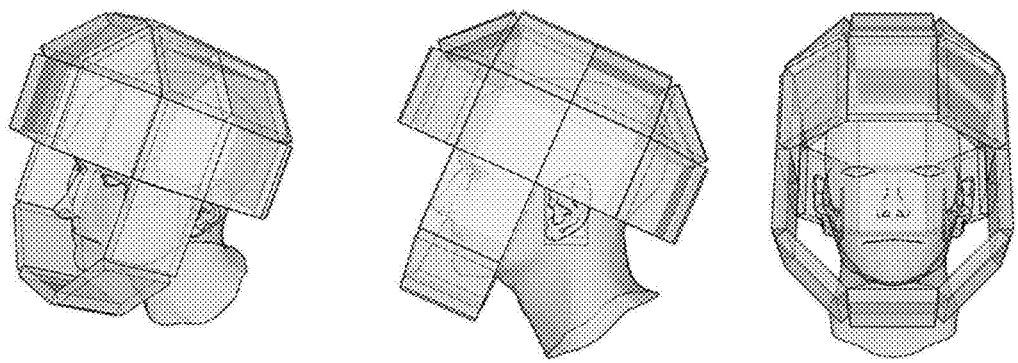

FIG. 22: Example of preferred embodiment in which the detection modules together form a structure composed of three parts: the central one is an elongated octagonal base prism whose sides facing the ears are formed by more modules than the other sides of the octagon, the upper one is a dome with a rectangular base that replaces the upper base of the prism, covering it, which exactly closes the previous prism and is therefore octagonal on the sides of the ears, and which is placed in the area corresponding to the upper part of the head when the PET imaging device is in use. And the third part is a lower part in the form of a ring or bridge perpendicular to the prism, which replaces the lower base of the prism, and which is a set of several modules arranged in a chain, which join two faces of the prism facing each other, and parallel to each other, and in a way that this lower part faces the chin of a subject when the device is in use. Each side of the octagonal prism or the dome may be formed by one or more detection modules. Together, the prism and dome form a shape similar to Johnson's solid called elongated square dome, also called diminished rhombi-cuboctahedron, except that the sides of the ears have been elongated in the nape-front direction and, therefore, the dome is not square but rectangular. Altogether, the prism and the dome have 17 faces: 5 rectangles, 8 squares (which could also be replaced by rectangles) and 4 triangles. The lower part, that is placed facing the chin, can be displaced towards the front half of the prism (so that it covers the lateral area of the head coinciding with the eyes) as seen in FIG. 22, or it can be centered with respect to the prism and the dome that covers the octagonal prism, so that it covers the central lateral part of the head. In FIG. 22, central drawing, this arrangement—which is not shown in the figures—would show the detection module of the lower part in contact with the half of each side of the modules immediately above, which constitute faces of the prism.

This configuration, with the lower part of the structure centered has the advantage that it allows to observe the central area of the brain, and in particular the hippocampal zone, entorhinal cortex and amygdala.

Figure 23:
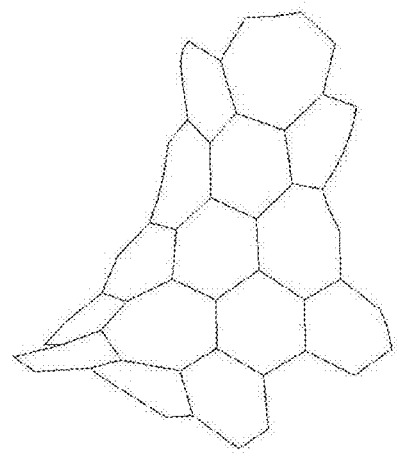

FIG. 23: Given that the neck has a surface with negative curvature such as a hyperboloid (a saddle on horseback) it is not easy to approach said surface by means of polygons. This figure shows the example of a preferred embodiment shown in the previous figure, but wherein, in the part of the imaging device disposed facing the chin, crystal blocks in the form of hexagons and hexagons are used.

Figure 24:
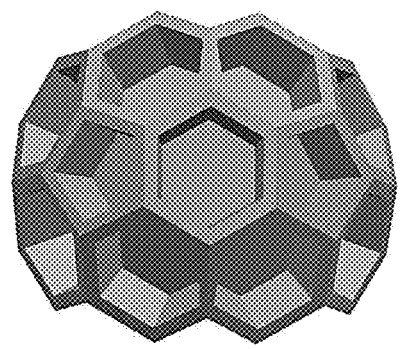

FIG. 24: example of a mechanical structure based on carbon fiber, on which the different modules with hexagonal, pentagonal, etc. sections, are placed. The thickness of the structure between crystal blocks is exaggerated in the figure so that it can be visualized, but obviously in the actual implementation it is minimal, to minimize the distance between scintillation crystal blocks and maximizing sensitivity.

Figure 25:
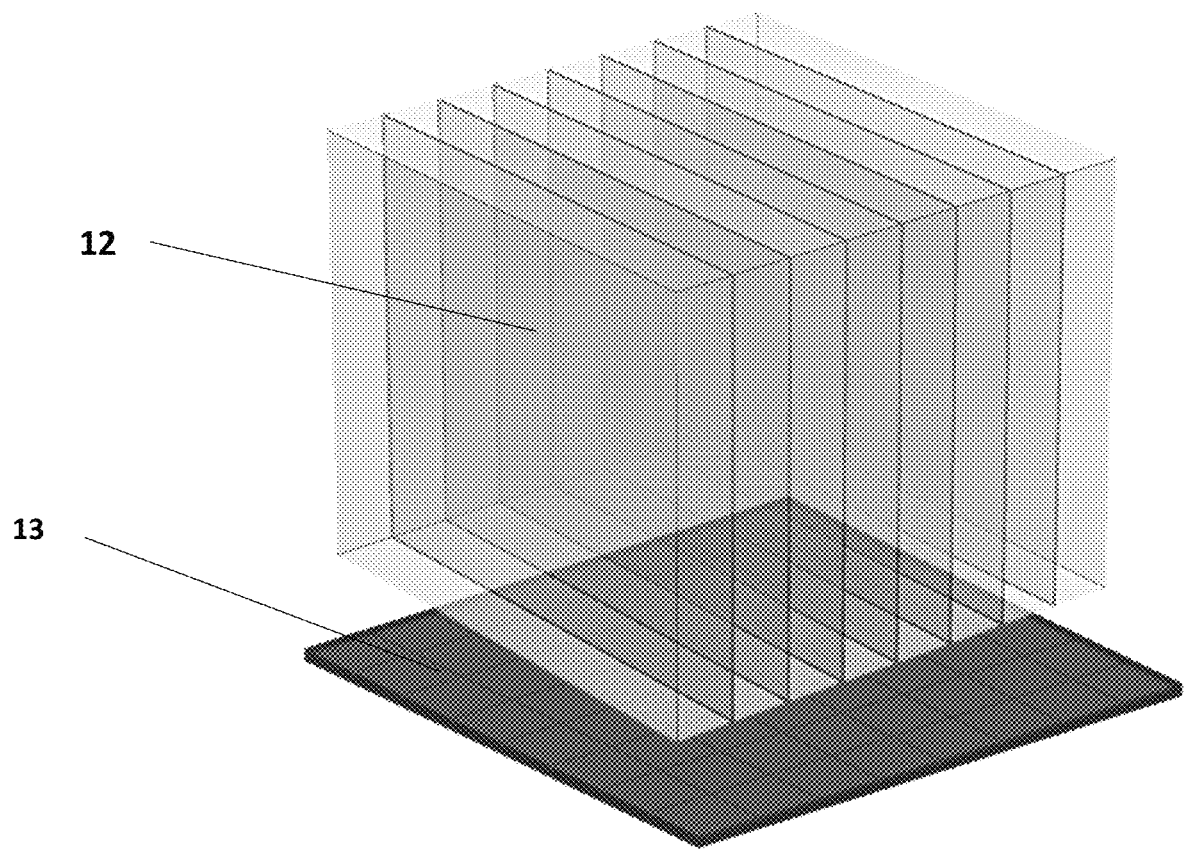

FIG. 25: This figure shows the crystal block when made out of multiple slabs or semi-monolithic crystals, that is with one dimension significantly larger than the other, coupled to a photosensor and readout electronics.

(12) crystal block
(13) photosensor array and readout electronics.

DETAILED DESCRIPTION OF THE INVENTION

The object of the present invention is a PET imaging device dedicated to the examination of the brain, which may be the one of a mammal such as a primate, and preferably it will be a human brain, for the diagnosis and monitoring of neurological diseases, maximizing sensitivity and at the same time minimizing the number of detectors used and, therefore, the cost, weight and complexity.

The sensitivity is optimized by means of a greater angular coverage of the detectors, which allows detecting the coincidence of gamma rays emitted in the area of the brain in opposite directions, such as it occurs in the emission events by PET radioisotopes.

Figure 1:
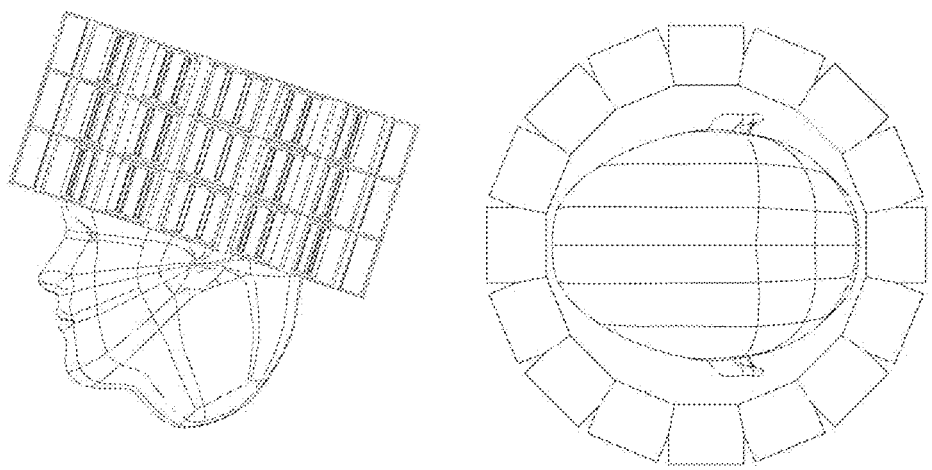
FIG. 1: shows a configuration of detection modules forming multiple rings, of circular section, belonging to the state of the art, compared with the morphology of the human head and in which an important separation between the detectors and the head can be seen.
Figure 2:
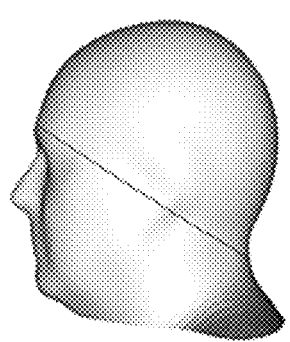
FIG. 2: Left: shows a real human head and the line on which the section to which the PET device should approach—in order to increase its efficiency—will be calculated. Right: Shows an ellipsoid representing the involute of a real human head.
Figure 2:
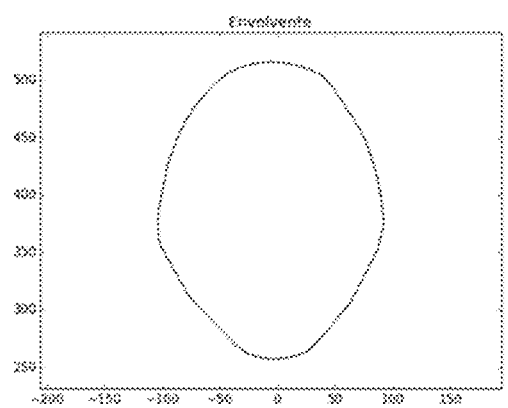

The Instituto Valenciano de Biomecánica (Valencian Institute of Biomechanics) (IBV) conducted a statistical study of the shape and size of the human head. The result is that the size varies significantly according to different nationalities and sexes, and individually within each country. However, a common feature is that the shape of the human head is not spherical but is narrower in the direction between the two ears, compared to the other two directions perpendicular to it (see FIGS. 1 and 2). This suggests the design of a PET imaging device with an elongated geometry to better adapt it to the shape of the human head. The object of the present invention is a PET device that meets these provisions, that is, maximum angular coverage to maximize sensitivity, and elongated shape, similar to the head, in particular the human head, placing the PET imaging device as close as possible to the brain, to minimize the number of detectors used. Another common feature is that the head is narrower in the front than in the back (FIG. 2 right).

An essential feature of the PET imaging devices of the invention is therefore that the gamma detection modules are arranged so that they can surround the head of the subject, together forming an elongated, non-spherical surface, to better adapt to the three-dimensional shape of the head, in particular the human head. This allows to obtain a maximum sensitivity while minimizing the number of detectors used and, therefore, the cost of the PET imaging device.

However, and given that the PET imaging device is designed for the diagnosis of neurological diseases, many patients will be elderly, and some of them, or younger ones may present mental illnesses, such as schizophrenia, it is critical for a correct examination that the patient is comfortable and that he/she can see, hear and breathe without any difficulty. On the other hand, the sizes and shapes of the heads differ on average between different continents and nationalities, and individually within each country, with total variability in the size of up to around 5%. Therefore, the proposed designs should allow a space between the image device and the head sufficiently loose to fit different sizes and shapes of heads.

The device of the present invention is a PET imaging device dedicated to the observation of the brain, characterized in that as a whole it has a structure with a shape capable of housing a head, comprising independent gamma ray detection modules, said detection modules comprise continuous scintillation crystal blocks of polygonal main section, in which the detection modules together form a hollow three-dimensional structure capable of circling the head, and said elongated three-dimensional structure having a major axis in the direction corresponding to the front-nape direction and a shorter axis in the direction corresponding to the straight line joining the ears, and the adjacent scintillation crystal blocks being arranged to fit laterally in an exact manner with each other throughout their entire thickness, building a mosaic, that is to say, without leaving gaps and without overlapping each other. Preferably, the adjacent scintillation crystal blocks are of the same thickness fitting laterally in an exact manner with one another throughout their entire thickness.

Figure 5:
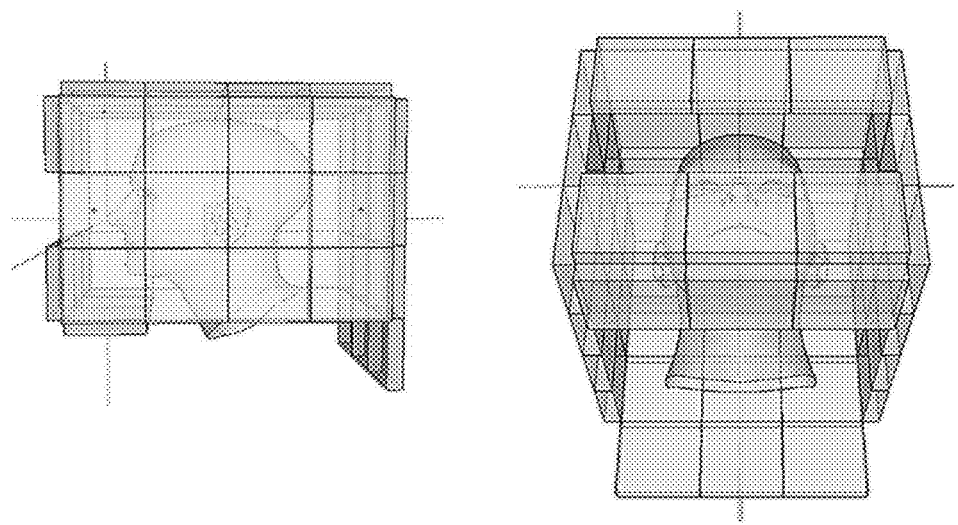
FIG. 5: shows an example of configuration of the PET imaging device in the form of a lying down, hollow prism with a square base. Said prism almost completely covers the head leaving only a hole for the neck and for the eyes. The sides corresponding to the lower area of the jaw only have detectors in that region, in order to leave a loose space for the neck. The rear or rear base has been completely covered with square detectors and has even been extended towards the back to increase sensitivity. The front base has been covered only partially, in the area of the chin and forehead, to allow the eyes a comfortable vision. The lower side of the prism, which corresponds to the area of the neck when the imaging device is in use, only has one fragment so that it forms an "L" with the front base of the prism. The position of the part of the L-shaped front base corresponding to the chin area is adjusted for each subject after having placed the PET imaging device on the head.

According to particular embodiments, in the PET imaging device, the detection modules have a square or rectangular shape, forming together a lying down, hollow, prism with a rectangular base (as shown for example in FIG. 5) capable of housing a head, the anterior base of said prism being in the front part of the structure that can be confronted to the face of a subject, and the rear base of the prism is in the area—corresponding to the back of the head-, is in the posterior part of the structure that can be confronted to the occipital bone; and optionally, the rear base can be extended with additional detection modules towards the area corresponding to the back when the device is placed on the head of a subject.

According to further particular embodiments, in the PET imaging device the detection modules have a square or rectangular shape, forming together a lying down, hollow, prism with a rectangular base capable of housing a head, the anterior base of said prism being at the front of the structure that can be confronted to the face of a subject, and the rear base of the prism is in the area that corresponds to the back of the head, at the back of the structure that can be confronted to the occipital bone, each side of said prism being covered with detectors with continuous crystal blocks of square section, so that each side of the prism that can be placed facing the neck, and the front base, are covered only partially, so that the neck fits loosely and does not obstruct the vision, while the rear base and all remaining sides of the prism are completely covered by detectors; and optionally, the rear base can be extended with additional detection modules towards the area corresponding to the back when the device is placed on the head of a subject.

For any of these described embodiments of the PET image device, in which the detection modules have a square or rectangular shape forming together a lying down, hollow, prism with a rectangular base, capable of housing a head, the anterior base of said prism being in the front of the structure that can be confronted to the face of a subject, and the posterior base of the prism being in the area that corresponds to the back of the head, at the back of the structure that can be confronted to the occipital bone, wherein the side of the prism that can be confronted to the neck when the imaging device is in use, and which is only partially covered with detection modules, forms with the front base of the prism a fragment thereof with an "L" form, and this L-shaped fragment corresponding to the chin area when the device is in use, is adjustable in position for each subject after having placed the PET imaging device on the head. In the position adjustment operation for a particular subject, the entire "L" shaped fragment can be displaced.

Figure 6:
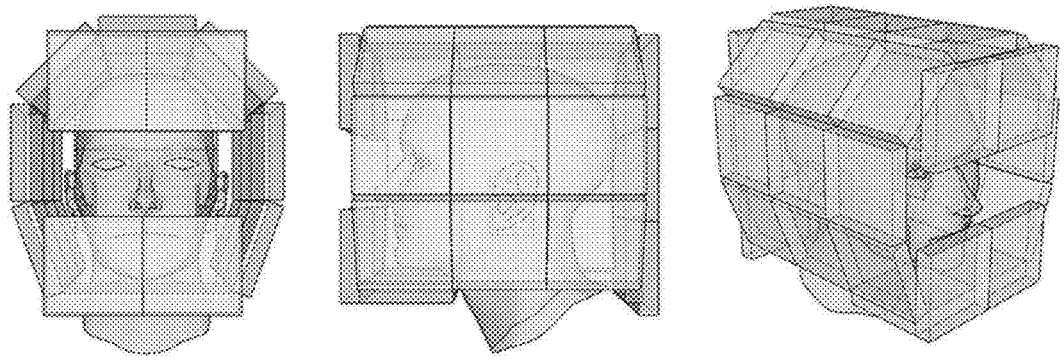
FIG. 6: shows an exemplary embodiment of detection modules with square scintillating continuous crystal blocks in the shape of an irregular prism with eight sides. The sides corresponding to the lower area of the jaw only have detectors in that region to leave a loose space for the neck. The rear or posterior base has been completely covered with square detectors. The front base has been covered only partially, in the area of the chin and forehead, to allow the eyes a comfortable vision.

According to further particular embodiments, the detection modules have a square or rectangular shape, forming together a hollow prism of bases of pentagonal, hexagonal, octagonal etc. section, capable of housing a head, the anterior base of said prism being at the front of the structure that can be placed in front of the face of a subject, and the other base of the prism on the back of the structure that would face the back of the head, that could be confronted to the occipital bone. An example of this embodiment is shown in FIG. 6, wherein the square continuous scintillating crystal blocks are arranged in the form of an irregular eight-sided prism. The sides corresponding to the lower area of the jaw only have detectors in that region to leave a loose space for the neck. The rear base has been completely covered with square detectors. The front base has been covered only partially, in the area of the chin and forehead, to allow the eyes a comfortable vision.

According to further particular embodiments, the PET imaging device may comprise triangular, square and rectangular shaped detection modules, which together form a hollow prism with a base in the form of a polygonal dome, for example square, pentagonal, hexagonal or octagonal dome.

According to additional particular embodiments, the detection modules have a square or rectangular shape forming together a hollow prism capable of housing a head, wherein polyhedral domes form the bases. In particular, for this alternative of the invention, the detection modules have a square or rectangular shape forming together an octahedral prism capable of housing a head, and with a base in the form of a square dome.

Figure 7:
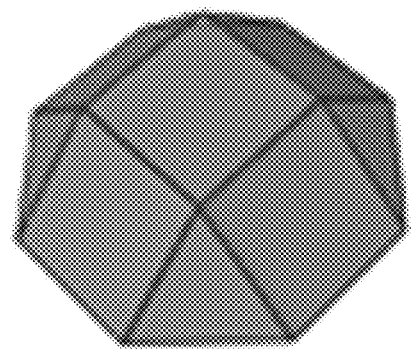
FIG. 7: shows an example of a base in the form of a square dome. This base adapts better to the shape of the back of the head. This base includes triangular scintillation crystal blocks. Other similar bases in the form of a pentagonal, hexagonal dome, etc., are also analogously put into practice.
Figure 8:
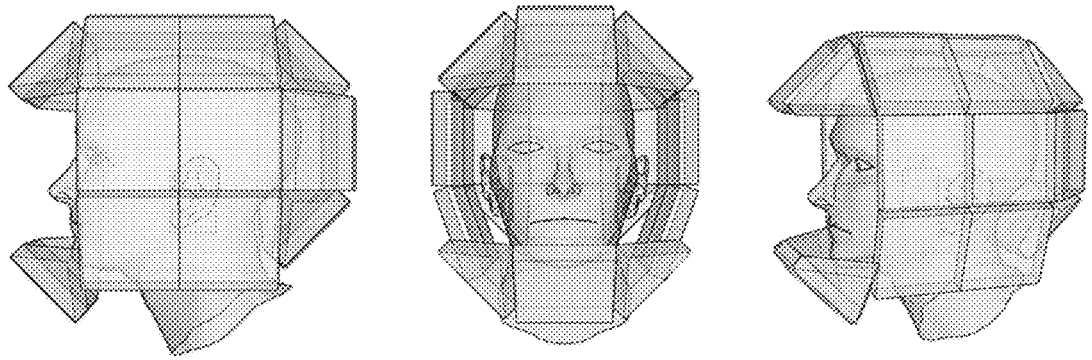
FIG. 8: shows an example of arrangement of square scintillating continuous crystal blocks in the form of an irregular eight-sided prism. The back has been completely covered by a square dome. Alternatively, other similar bases are used in the form of a pentagonal, hexagonal dome, etc. Likewise, the front part has also been covered, although only partially, in the area of the chin and the forehead, to allow the eyes a comfortable vision, by means of a base of the prism in the form of a square dome.

In another embodiment of the present invention, the bases of the prisms have a polygonal dome shape. An example of a square dome is shown in FIG. 7. This base adapts better to the shape of the back of the head (FIG. 8), allowing to significantly decrease the number of continuous scintillation crystal blocks used. However, it has the disadvantage of adding continuous scintillation crystal blocks of triangular surface. Likewise, the front part has also been covered, although only partially, in the area of the chin and the forehead, to allow the eyes a comfortable vision, by means of a base in the form of a square dome. Other similar bases in the form of a pentagonal, hexagonal dome, etc., can also be implemented analogously by means of introducing crystal blocks of irregular polygonal section.

Figure 9:
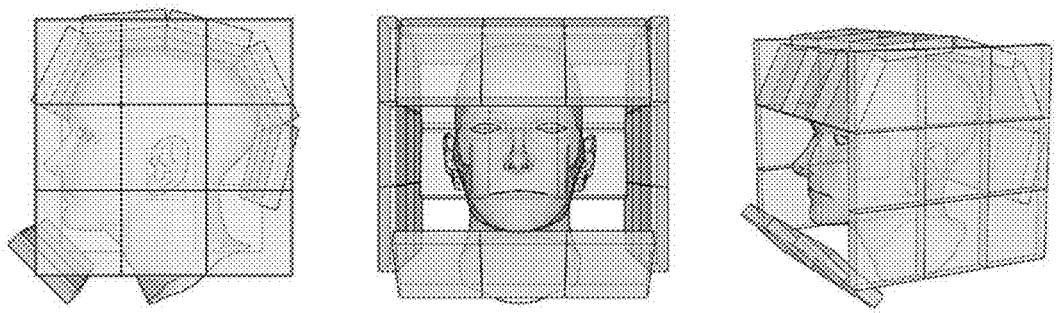
FIG. 9: shows a configuration example of the PET imaging device in which the bases of the hollow prism are parallel to the ears. In this case the prism is formed by eight sides (octagonal prism), including the side corresponding to the subject's chin and also including the absent sides of the neck and the eye area. The bases, instead of being formed by irregular decagons, are formed by a large square that is constituted by 9 detectors.

According to additional particular embodiments of the PET imaging device, the detection modules form a hollow prism the lateral faces of which are the faces that can be arranged between the nape and the forehead of a subject, and the bases of the prism are the faces that can be arranged parallel to the ears, as shown in FIG. 9. In the example the prism is formed by eight sides (octagonal prism), including the side corresponding to the chin and the absent sides of the neck and the eye area. The bases, instead of being formed by irregular octagons, are formed by a large square that is constituted by 9 detectors.

Forms that approach the sphere starting from flat surfaces can be achieved by hexagons and pentagons as in the truncated icosahedron. However, the size of the truncated icosahedron is limited by the size of the edge of the faces, and is given by the following formula, for an edge of unit size:

$$r_5 = \frac{1}{2}\sqrt{\frac{1}{10}(125 + 41\sqrt{5})}$$

$$r_6 = \frac{1}{2}\sqrt{\frac{3}{2}(7 + 3\sqrt{5})}$$

where $r_5$ y $r_6$ are the radius to the center of the pentagons and hexagons, respectively. For an edge of size a we must multiply $r_5$ and $r_6$ by the length of the edge.

Bearing in mind that continuous scintillation crystals are manufactured from cylindrical ingots with a maximum diameter of around 70 mm in the case of LSO, or 135 mm in the case of BGO, the maximum edge of a regular hexagon (corresponding to half of the ingot diameter) will be 163 mm. This limits the truncated icosahedron shape to the BGO case, and consequently the LSO and its variants cannot be used. The family of LSO crystals has the characteristic of emitting a large amount of light and a very short emission time with respect to the BGO, which are very suitable for the precise determination of the time of flight (TOF: Time of Flight).

Figure 10:
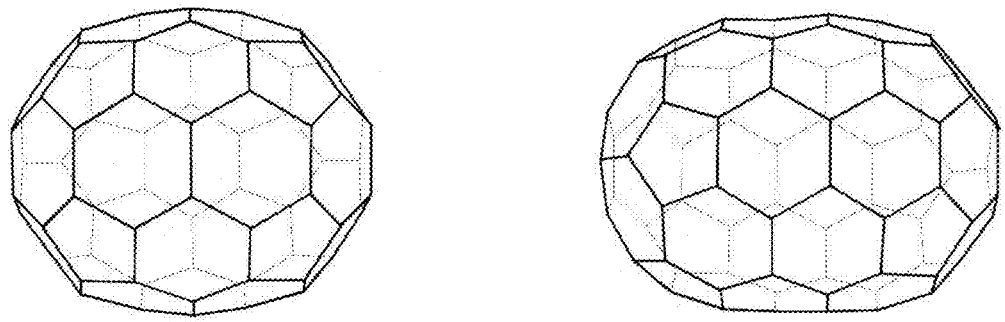
FIG. 10: shows examples of elongated shapes with a greater or lesser number of faces, starting from regular pentagons, regular and irregular hexagons. This configuration is better suited to the shape of the head than the truncated icosahedron or any other shape that mimics the sphere. The shape on the left contains 70 vertices and the one on the right contains 80. The configuration on the left contains 12 regular pentagons, 10 regular hexagons, 15 irregular hexagons, and 105 edges. The configuration on the right contains 12 regular pentagons, 10 regular hexagons and 20 irregular hexagons and 120 edges, and has symmetry of the D5d group.

Alternatively, in another embodiment of the present invention, the PET imaging device has elongated shape starting from 12 flat surfaces of pentagonal section and different number of flat surfaces of—regular and irregular—hexagonal section, of arbitrarily large size. In FIG. 10 two examples are shown. In the example on the left, there are 70 vertices, 12 pentagons, 15 regular hexagons and 10 irregular hexagons, that is, 37 faces in total. This form, in which it is critical to add irregular hexagons, has two important advantages with respect to the truncated icosahedron (the soccer ball): 1) it has an elongated shape that adapts better to the head; 2) it can be made arbitrarily large. Similarly, the configuration on the right of the same FIG. 10 contains 12 regular pentagons, 10 regular hexagons and 20 irregular hexagons and 120 edges, and has symmetry of the D5d group.

Alternatively, starting from 12 pentagons and different number of regular and irregular hexagons it is possible to put into practice practically any elongated shape.

Figure 11:
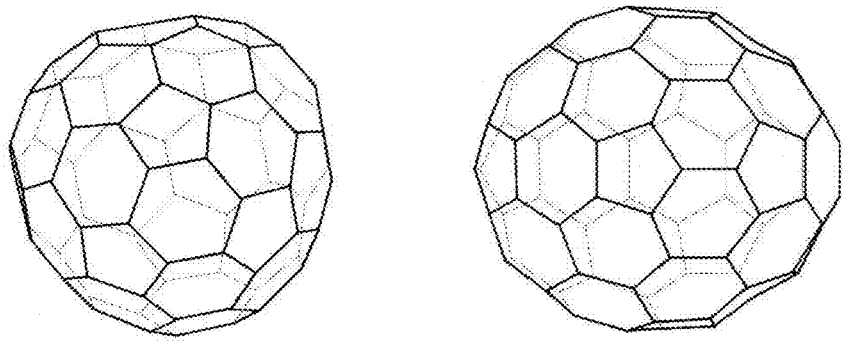
FIG. 11. It shows examples of hollow three-dimensional structures with elongated and narrower shapes in the anterior part corresponding to the area of the forehead, when the device is in use, than in the posterior part corresponding to the nape area when the device is in use, being therefore capable of being adapted to the shape of the human head. These structures are made starting from regular pentagons, regular and irregular hexagons. These configurations adapt perfectly to the shape of the head, narrower in the front than in the back. The shape on the left contains 76 vertices, having the symmetry group Ta, and the one on the right contains 84 vertices.
Figure 12:
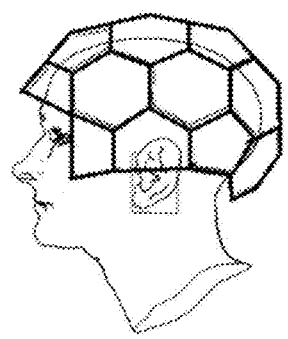
FIG. 12: shows an example of PET image device of the previous figure perfectly adapted to the shape of the head.
Figure 13:
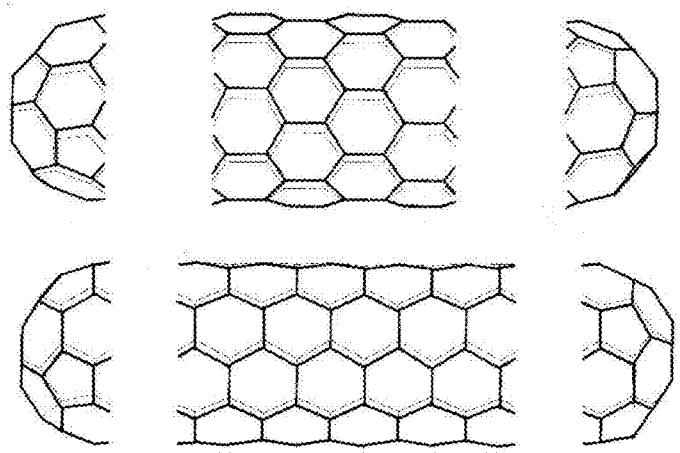
FIG. 13: shows an example of a hexagonal arrangement in "zig-zag" or "armchair" forming a cylinder of arbitrary length to which it is attached, in order to close the cylinder on both sides a hemisphere formed by regular hexagons and pentagons, such as in a truncated icosahedron. Alternatively, the cylinder is closed by a dome as in FIG. 7.

Alternatively, another embodiment of the present invention relates to a PET imaging device with an elongated shape, which is also narrower in the forehead area than in the rear part, adapting even more to the shape of the head. In FIG. 11 two examples are shown. The example on the left contains 76 vertices, having the symmetry group Ta, and the one on the right contains 84. Starting from 12 flat surfaces of pentagonal section and different number of flat surfaces of hexagonal, regular and irregular, section, these and other shapes of arbitrarily large size can be put into practice. In FIG. 12, the arrangement of continuous crystal blocks of the PET imaging device, perfectly adapted to the shape of the head, is shown.

Starting from regular polygons of a few types can also be used to construct Archimedean solids other than the truncated icosahedron, some of which could be used as helmets if only half the solid is used, for example: truncated Icosidodecahedron or the dull Dodecahedron.

Starting from regular polygons of a few types, Johnson's solids can also be constructed, some of which could be used as helmets if the base is removed (the largest polygon, octagon or decagon), for example: elongated square dome, elongated pentagonal dome, elongated pentagonal roundabout, gyro-elongated square dome, gyro-elongated pentagonal dome, gyro-elongated pentagonal roundabout, pentagonal ortho-roundabout-dome, (Ortocupularrotonda), pentagonal gyro-dome-roundabout, diminished rhomboicosahedron, diminished paragyroid rhomboicosahedron, and diminished metagiroide rhomboicosahedron.

Also starting from simple irregular polygons one can build the Catalan solids, some of which could be used as helmets if only half of the solid is used, for example: deltoidal hexecontahedron and pentagonal hexecontahedron.

These configurations from polygons such as pentagons, regular hexagons and irregular hexagons, etc., are not easy to build. To this purpose, according to a particular embodiment, a mechanical system based on a rigid honeycomb like structure is provided (FIG. 24) where each one of the detection modules will be housed in their pre-established position and orientation. Each honeycomb cell has the proper geometry and size to complete the final configuration of the device. The matrix also incorporates a mechanical interface to be able to link this element with other possible components of the system (positioner of the detector system with respect to the patient, support, protective or embellisher casing). The matrix is opaque to visible light, to prevent light from entering the cell, but the light is low density to avoid unwanted interactions (scatter, Compton, attenuation) with radiation from the patient.

The PET imaging device of the present invention, in addition to the gamma ray detection modules, comprises the electronics for the acquisition of data coming from the detection modules, the electronics of the temporal coincidences "trigger", a computer for the data acquisition and storage and computer programs for reconstruction and visualization of the image from the data.

Figure 3:
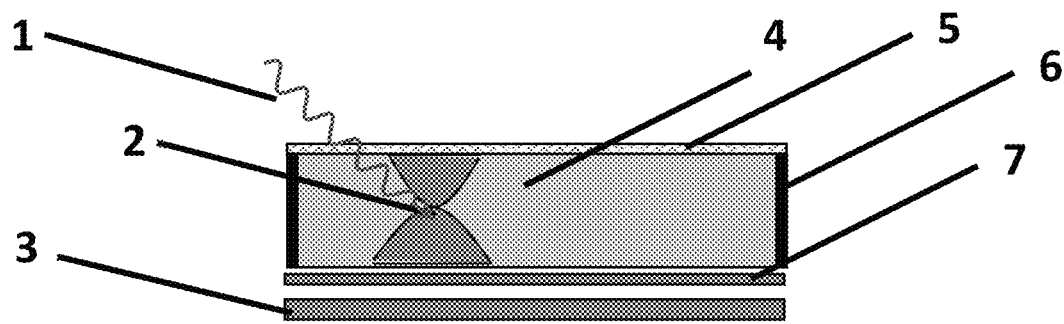
FIG. 3: illustrates an embodiment of the detection module, comprising a continuous scintillation crystal block, a set of photo-detectors, the reading electronics, and a mechanical encapsulation of the whole assembly. 1: gamma ray, 2: scintillation light emission point; 3: photo-sensor array; 4: scintillation crystal block; 5: treatment of the glass entrance surface, preferably retroreflector; 6: treatment of the lateral surface of the glass by means of specular reflector, black paint or other absorbent paint, or a combination thereof; 7: light diffuser or light guide.

Each detection module comprises a continuous scintillation crystal block, also called monolithic crystal block, a set of photo-detectors for the collection of the light emitted by the scintillation crystal block after the interaction of the gamma ray thereon, the reading electronics of said photo-detectors, and optionally, a mechanical encapsulation of the whole assembly, as shown, by way of example, in FIG. 3. In this particular embodiment shown in this figure at least one of the crystal faces is covered at least in part by the set of photo-detectors.

Figure 4:
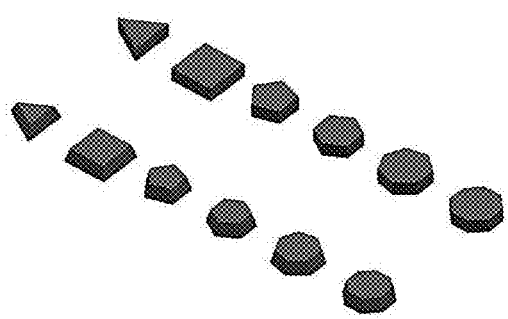
FIG. 4: illustrates embodiments of the shape of the continuous scintillation crystal blocks of the detection modules, with polygonal main section. Prisms of triangular, square, pentagonal, hexagonal, heptagonal and octagonal section. Pyramids truncated by a cut parallel to the base of triangular, square, pentagonal, hexagonal, heptagonal and octagonal section.

On the other hand, it must be taken into account that the photo-detectors must be placed on flat surfaces of the continuous scintillation crystals, or of light diffusers or light guides attached to said flat surfaces. The reason is that the photodetectors used in the present invention, both solid state photodetectors and position sensitive photomultipliers, have flat entry surfaces. Therefore, scintillation crystal blocks with curved surfaces are not used in the PET device of the invention since they would not fit perfectly to the flat surface of the photo-detectors. In addition, it is much more complicated to build continuous crystal blocks with curved surfaces. Therefore, each of said crystal blocks has a polygonal main section, for example, in the form of a polygonal prism or truncated polygonal pyramid (see, by way of example, FIG. 4). In general, the width of the crystal block will be the same for all scintillation detectors regardless of their polygonal shape.

In a preferred configuration, each detection module has a single face where the photo-detectors are located. This face is covered to the maximum by photo-detectors in order to optimize the resolution in impact position of the gamma rays in the crystal block, the time resolution and energy resolution. In said preferred configuration, the surface opposite to the one of photo-detection is completely polished and covered by a retroreflector. The detection modules can be arranged so that the gamma rays enter on the opposite side to the photo-detectors or, alternatively, on the side where the photo-detectors are located.

It should also be borne in mind that virtually all photo-sensors have a photosensitive surface of square or rectangular section, especially solid-state photo-sensors, and it is therefore very convenient that the continuous scintillation crystal blocks also have a square or rectangular section where the photo-sensors are placed. In this way, the non-sensitive (dead) zones are minimized and therefore the light collection is maximized, optimizing the energy resolution of the gamma ray and its impact position on the crystal block.

Furthermore, to maximize the sensitivity of the detector it is critical that there are no gaps between the scintillation crystal blocks so that the gamma rays do not escape between said gaps and be therefore not detected. At the same time, it is important to avoid overlapping between the scintillation crystal blocks, i.e. some crystal blocks are mounted on others, to minimize the cost of the PET imaging device. Therefore, it is very convenient that all the lateral faces of the crystal blocks are exactly coupled to their neighbouring crystal blocks.

Therefore, the PET devices of the invention have in common that the different continuous scintillation crystal blocks do not leave gaps among them by which the gamma rays can escape without being detected, except the minimum width of the encapsulation in case there is an encapsulation that contains each module. Therefore, an essential feature of the present invention is that the scintillation crystal blocks have the shape of polygons, preferably of the same thickness, fitting laterally in an exact manner with one another throughout their entire thickness, building a mosaic, i.e, without leaving gaps and without overlapping each other.

It should also be borne in mind that it is not appropriate for the manufacture of a PET imaging device that the shape of the modules be different for each detection module. Optimal is that all the detection modules are identical to each other to facilitate the manufacture of them in series. It would also be assumable in manufacturing, that there only were be two or three types of different detection modules. This is important not only for the manufacture of the detection modules but also for the method of determining the impact point of the gamma ray in the crystal block, which is different for each type of module. Therefore, if an embodiment consists of crystal blocks in many different forms, it would be necessary to develop an algorithm for determining impact point of the different gamma ray for each crystal block.

Each detector module can be enclosed by an encapsulation to immobilize the module components (continuous crystal block, photo-detector and associated electronics) in their nominal position, avoiding that light be introduced inside the detector module and at the same time dissipating the heat generated by the detector module components.

The materials to be used for said components can be of different nature (such as polymers or metals), and their selection will depend on factors inherent to the selected configuration and the density of the detection module elements, but preferably polymeric materials are used due to their scarce interaction with the patient emitted radiation.

The manufacture of the components is carried out by any method suitable to the chosen materials (machining, injection, casting, printing, sintering) but is preferably carried out by 3D printing or sintering due to the low production cost for small series, the variety of available materials and finishings, as well as the limited restrictions of these methods in terms of geometric design characteristics and needed tolerances.

All commercial and academic PET use detection modules (and scintillation crystals) of square or rectangular section. Furthermore, in said modules the light produced by the impact of the gamma rays on the crystal is directed towards a single photo-detection surface, of square or rectangular section. Said surface of square or rectangular section can be completely covered by photo-detectors of square section to maximize the resolution in position, in energy and time.

However, it is not possible to completely cover flat surfaces of triangular, pentagonal, hexagonal, or heptagonal section, of the continuous scintillation crystal blocks that are used in the present invention, by commercially available square section photo-detectors. This involves a deterioration in the resolution in position, energy and time. To overcome this difficulty that has not been raised up to now, the present invention provides different solutions that are developed below.

Figure 14:
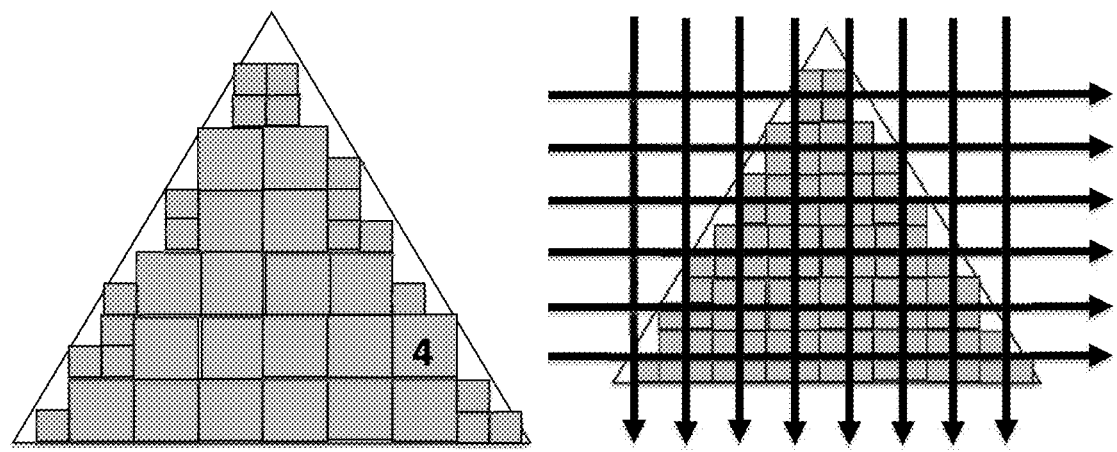
FIG. 14: Left. It shows an example of the disposition of the photo-detectors of two sizes (in this case they are square photo-detectors in which one has sides of half the size of the other) to cover a larger area of the continuous scintillating crystal block with triangular section, without exceeding this one, since it would collide with the photo-detectors of adjacent crystal blocks. It has to be noted that all the large photo-detectors are aligned with each other forming a matrix to facilitate reading by means of rows and columns, as shown in the figure on the right. Analogous arrangements are made in the case that the surface of the scintillation crystal block were in the form of a pentagon, hexagon, etc.

An object of the present invention is the use of two sizes of photo-detectors, for example, squares of 6 and 3 mm, as shown in FIG. 14 to maximize the area covered by the detectors without exceeding it, since it would collide with the photo-detectors of adjacent continuous crystal blocks. It has to be noted that all large-sized photo-detectors are aligned with each other forming a matrix to facilitate reading by rows and columns, as shown in the next figure. Analogous arrangements are made in the case that the surface of the scintillation crystal block is in the form of a pentagon, hexagon, etc.

Alternatively, an electronic method is available to read and digitize each and every one of the photo-detectors Individually by, for example, an ASIC (Application Specific Integrated Circuit), it is possible to cover a larger area of the scintillating crystal block when the restriction of alignment in rows and columns disappears. Analogous arrangements are made in the case that the surface of the scintillation crystal block were in the form of a pentagon, hexagon, etc.

Alternatively, the squares of the photo-detectors may protrude if the adjacent surface is a square or rectangular surface. This can be done by using slightly thicker crystal blocks (for example, as shown in FIG. 16).

The photo-detectors can be arranged to completely cover the surface of the continuous scintillation crystal block surpassing the surface area of the triangle. The collision with the photo-detectors of adjacent crystal blocks, if the latter are square or rectangular in section, can be avoided by increasing the thickness of the triangular scintillation crystal block (FIG. 18) the glass on the right is slightly shifted (a few millimetres) towards the outside (FIG. 19) or by using a thick sheet of material transparent to light, which acts as a light diffuser or as a light guide (FIG. 20). Analogous arrangements are made in the case that the surface of the scintillation crystal block were in the form of a pentagon, hexagon, etc. In general and for any embodiment, the collision with the photo-detectors of adjacent crystal blocks can also be avoided regardless of the shape of the polygon by using light guides in the form of truncated pyramids (fish tail) with a wider base in the part of the scintillation crystal block (as shown for example in FIG. 21) and with the polygonal form of said crystal block. Said narrowed light guides can be obtained starting from optical fibers.

The conditions fulfilled by the PET devices of the invention are the following: 1) they are elongated shape, adapted as much as possible to the shape of the head, constituted from independent detection modules, with the greatest possible angular coverage of the brain; 2) maximum proximity of the detection modules to the head, respecting the comfort of the patients; 3) gamma ray detection modules composed of continuous scintillation crystal blocks with flat surfaces; 4) maximum three different forms of scintillation crystal blocks; 5) exact coupling between the lateral surfaces of the scintillation crystal blocks; and 6) surfaces that can be covered almost completely with square surface photo-sensors.

The PET imaging device according to any of the alternatives described above, may comprise a protective element capable of being mechanically or manually operated to produce a complete adaptation of the PET imaging device to the shape of an object, such as a head, the image of which is to be obtained, and to immobilize said object.

Said protective element can be selected between an air cushion system, attached to the set of detection modules, and a system of elastic containers, filled with small spherical particles or with any other geometry, of low density.

The movement of the head during the acquisition time generates artefacts and degrades the image quality. Two methods are proposed in the present invention to reduce such an effect by introducing an element between the three-dimensional structure of the detector array and the patient's head, with the ability to dynamically adapt to both.

The present invention also relates to a method to carry out an image acquisition with a PET imaging device defined above.

The present invention also relates, according to particular embodiments, to a method for carrying out an image acquisition with a PET imaging device defined above, comprising arranging a protective element between the PET imaging device and the object, such as a head, the image of which is intended to be obtained, such that said protective element when being mechanically or manually operated produces a complete adaptation of the PET image device to the shape of the object of which is intended to be obtained. The protective element can be an air cushion system or a system of elastic containers, as defined above.

In the case of the air cushion system, attached to the three-dimensional structure of the detector assembly and located between said three-dimensional structure and the patient's head, which can be operated by means of a manual or automated inflation system, which allows filling the separation between the three-dimensional structure and the head, immobilizing the patient's head inside the structure.

In the case of the bag system, for example two, or elastic containers, filled with small spherical particles or with any other geometry, of low density—to avoid artefacts—, they can be slightly mechanically pressed to the front and side of the patient's head to, then they are pressed under vacuum, using a pump included for that purpose, which causes these bags or containers to faithfully adopt the shape of the patient's skull, preventing it from moving or rotate with regard to the original position in which it was at the time the vacuum was applied.

EXAMPLES OF PREFERRED EMBODIMENT

Example 1

In a first preferred embodiment of the brain PET imaging device, the continuous scintillation crystal blocks together form an 8-sided prism of elongated shape, and which can be arranged inclined along the head, as shown in FIG. FIG. 22 This prism is closed at the top by a dome composed of 8 square-section crystal blocks and 4 triangular-section crystal blocks. At the bottom, the prism is closed by a bridge formed by 5 square section scintillation crystal blocks around the chin.

The scintillation crystal blocks are BGO (Bismuth Germanate, $Bi_4Ge_3O_{12}$) and with truncated pyramidal form with a square section, 20 mm thick and 95×95 $mm^2$ base size. The truncation of the pyramid is determined by the shape of the prism in such a way that the sides of the crystal blocks fit perfectly with each other to prevent gamma rays from escaping.

The base of each crystal block is completely covered with SiPM-type photo-detectors of 6×6 $mm^3$ size. All the electronic signals produced in the photo-detectors are read by rows and columns configuration. In the case of the scintillation crystal blocks with triangular section, the photodetectors are placed as in FIG. 16 and a light diffusing sheet or a light guide is placed between the crystal block and the photo-detectors as shown in FIG. 20 On the opposite side to the photo-detectors, a retro-reflector is placed to maximize the detection of light while preserving its original distribution.

Example 2

In a second preferred embodiment, the continuous scintillation crystal blocks are LSO (Lutetium Oxi-Orthosilicate doped with Cerium). All the crystal blocks have a 20 mm width. 5 crystal blocks have a regular hexagonal section of 35 mm edge. 6 crystal blocks have a pentagonal section of the same edge. 10 crystal blocks have an irregular hexagonal section with 4 edges of 35 mm and two slightly longer edges. This shape and size of the crystal blocks has the advantage of maximizing the size of the LSO ingot. All these crystal blocks are joined together to form an elongated structure around the patient's head as shown in FIG. 12.

The photo-detectors are of 3×3 $mm^2$ size and the signals produced by them are read individually through an ASIC that digitizes both intensity and time. This allows obtaining time of flight information, obtaining a better image quality.

The invention claimed is:

1. A PET imaging device for the observation of a brain, which has, as a whole, a hollow three-dimensional structure with a shape capable of housing a head, the PET imaging device comprising a plurality of independent gamma ray detection modules that together form a structure capable of surrounding the head, said detection modules comprise continuous scintillation crystal blocks, wherein "continuous" means that the crystal blocks can be continuous in one or in two directions, wherein each of the continuous scintillation crystal blocks has a polygonal main cross-section, and wherein said structure is an elongated structure having a major axis in a direction corresponding to the front-nape direction and a shorter axis in a direction corresponding to a straight line joining ears on the head, and the continuous scintillation crystal blocks are positioned adjacent to fit laterally in an exact manner with each other throughout their entire thickness, building a mosaic, without leaving gaps between adjacent crystal blocks and without overlapping each other.

2. The PET imaging device according to claim 1, wherein the main cross-section of each of the scintillation crystal blocks has a square or rectangular shape, and wherein the structure formed from the scintillation crystal blocks is a hollow, rectangular base prism, an anterior surface of said prism, being in a front part of the structure, that can be confronted to a face of a subject, and a rear surface of the prism, being in a posterior part of the structure that can be confronted to an occipital bone of the subject.

3. The PET imaging device according to claim 2, wherein each side of said prism is covered with detectors with a square main cross section; an insertion side of said prism, the insertion side having an opening through which the head may be inserted, being covered only partially, such that the neck fits loosely; the anterior surface being, covered only partially, such that the vision of the subject is not obstructed, and the back base and all remaining sides of the prism are completely covered by the detection modules.

4. The PET imaging device according to claim 2, in which the rear base has been extended with additional detection modules towards an area corresponding to a back of the subject when the device is placed on the head of the subject.

5. The PET imaging device according to claim 2, wherein an insertion side of the prism is only partially covered with detection modules, wherein the insertion side forms with a lower portion of the anterior surface of the prism a fragment thereof in the form of "L", and this L shaped fragment, that corresponds to a chin area of the subject when the device is in use, is adjustable in position for each subject after the PET imaging device has been placed on the head.

6. The PET imaging device according to claim 1, wherein the main cross-section of each of the scintillation crystal blocks is square or rectangular shaped, and wherein the structure formed by the detection modules is a hollow prism with a base of pentagonal, hexagonal, or octagonal section, an anterior base of said prism being on a front part of the structure capable of being confronted to a face of a subject, and the posterior base of the prism is at a back of the structure that would be facing a rear part of an occipital bone of the subject.

7. The PET imaging device according to claim 1, comprising detection modules having scintillation crystal blocks wherein the main cross-section is triangular, square, rectangular shape, or combinations thereof, and forming together a hollow prism with a polygonal dome shaped base.

8. The PET imaging device according to claim 7, wherein a shape of the dome is selected from square, rectangular, pentagonal, hexagonal or octagonal.

9. The PET imaging device according to claim 8, wherein the structure includes three parts: a central part which is configured as an elongated octagonal based prism, the sides of the central part are configured to face ears of a subject and are formed by more modules than the other surfaces of the octagonal based prism, an upper part is a rectangular base dome that defines an upper base of the octagonal based prism, covering it and closing the prism wherein the upper part is arranged in the area corresponding to an upper part of a head of the subject when the PET imaging device is in use, and a third part is a lower part of the structure in a ring or bridge connected to the central part perpendicular to the prism, and the third part defined a lower base of the prism, and a set of several detection modules arranged in a chain which join two faces of the prism confronted and parallel to each other, and the third part is configured such that it faces a chin of a subject when the device is in use.

10. The PET imaging device according to claim 9, wherein the lower part which is placed facing the chin is shifted towards an anterior half of the prism or is centered with respect to the prism and the dome covering it, such the lower part is capable of covering a central lateral portion of the head.

11. The PET imaging device according to claim 9, wherein the detection modules form an octagonal base hollow prism which in the part that is to be placed on the upper part of the head has the form of a square or rectangular dome, and the lower part that is to be disposed opposite the chin is covered with crystal blocks with the form of heptagons and hexagons.

12. The PET imaging device according to claim 8, wherein the detection modules have a square or rectangular shape, forming together a lying down, hollow, octahedral prism and with a square or rectangular dome shaped base.

13. The PET imaging device according to claim 1, wherein the detection modules form a prism, the lateral faces of which are capable of being arranged between a nape and a forehead of a subject, and the bases of the prism are the faces capable of being arranged parallel to the ears.

14. The PET imaging device according to claim 13, wherein the prism is formed by
eight sides, the eight sides including:
two sets of 3 adjacent sides, each set configured to face one of the ears on the head, and forming an interior angle between adjacent sides corresponding to an interior angle of an octagon, these two sets are separated by
a first side, forming interior angles with the adjacent sides which correspond to the interior angle of an octagon, and capable of facing an upper part of the head,
a second side, parallel to the first side, forming interior angles with the adjacent sides which correspond to the interior angle of an octagon capable of facing the lower part of the chin, and comprising a gap for placing the PET over the head,
an anterior base facing a neck of the subject; and
a posterior base facing an ocular area of the subject,
and the bases are square shaped and are made up of several detectors.

15. The PET imaging device according to claim 1, wherein the detector modules form a hollow three-dimensional structure having an elongated shape comprising 70 vertices or 80 vertices, the structure having $D_{5d}$ symmetry, and the detector modules having flat surfaces wherein at least a portion the detector modules have a pentagonal or hexagonal cross-section, regular or irregular.

16. The PET imaging device according to claim 1, wherein the detector modules form a hollow three-dimensional structure having an elongated shape that is further narrower in an anterior part, corresponding to a forehead of a subject when the device is in use, than in a rear part corresponding to a nape area of the subject, when the device is in use, such that it is capable of being adapted to the shape of a head.

17. The PET imaging device according to claim 16, wherein the detector modules form a hollow three dimensional structure comprising 76 vertices or 84 vertices, the structure having Ta symmetry, and the detector modules having flat surfaces, wherein at least part of said detector modules have a pentagonal or hexagonal, regular or irregular, cross-section.

18. PET imaging device according to claim 1, which further comprises a mechanical matrix structure opaque to visible light, rigid, honeycomb like, wherein each of the detector modules are housed in a pre-set position and orientation; and a mechanical interface for connecting a module to the other ones.

19. The PET imaging device according to claim 1, that comprises continuous scintillation crystal blocks of the same width for all of the detectors, regardless of their polygonal shape.

20. The PET imaging device according to claim 1, comprising detection modules of two different sizes.

21. The PET imaging device according to claim 1, wherein each detection module has a unique face where the photosensors are located and such that a surface opposite to photo detection is completely polished and covered by a retro reflector.

22. The PET imaging device according to claim 1, comprising a light diffusing sheet or a light guide between each continuous scintillation crystal block and photo detectors.

23. The PET imaging device according to claim 1, comprising a light guide, between each continuous scintillation crystal block and the photo detectors, in the form of truncated based pyramids with a base wider at the portion of the scintillation crystal block, and with the shape of the crystal block polygon, to prevent the photo detectors from adjacent crystal blocks from colliding with each other.

24. The PET imaging device according to claim 1, wherein the detection modules are arranged so that gamma rays enter the face opposite the photo detectors.

25. The PET imaging device according to claim 1, which comprises a protective element capable of being mechanically or manually actuated and capable of producing a complete adaptation of the imaging device to a shape of an object, the image of which is to be obtained, and to immobilize said object.

26. The PET imaging device according to claim 25, wherein the protective element is selected from an air cushion system, attached to the array of detection modules, and a system of elastic containers, filled with particles.

27. A method for obtaining images with a PET imaging device dedicated to observation of a brain of a subject, which has a structure with a shape capable of housing a head of the subject, the method comprising the steps of detecting gamma rays within independent gamma rays detection modules, said detection modules comprise continuous scintillation crystal blocks of polygonal main cross-section, wherein:
- the detection modules define a hollow three-dimensional structure capable of receiving the head,
- the elongated three-dimensional structure has a major axis in the direction between a front of the head and a nape of the subject,
- the elongated three-dimensional structure has a shorter axis in the direction corresponding to a straight line between ears of the subject, and the adjacent scintillation crystal blocks are positioned adjacent to each other to fit laterally in an exact manner with each other throughout their entire thickness, building a mosaic, without leaving gaps between adjacent crystal blocks and without overlapping each other.

28. The method according to claim 27, comprising providing a protective element between the PET imaging device and an object the image of which is to be obtained, such that said protective element upon being mechanically or manually actuated produces a complete adaptation of the PET image device to a shape of the object.

29. The method according to claim 28, wherein the protective element is an air cushion system, attached to the array of detection modules, which by using an inflation system fills the gap between the PET image device and the object the image of which is to be obtained.

30. The method according to claim 28, wherein the protective element is a system of elastic containers, filled with particles that upon being mechanically pressed cause adaptation of the PET imaging device to the shape of the object the image of which is to be obtained.

* * * * *